United States Patent
Salvucci et al.

(10) Patent No.: US 6,464,656 B1
(45) Date of Patent: Oct. 15, 2002

(54) DYNAMIC ARM SLING

(76) Inventors: Angelo Salvucci, 1679 Franceschi St., Santa Barbara, CA (US) 93105; Gary Bradley; Christopher Proctor, both of 536 E. Arrellaga St., Santa Barbara, CA (US) 93103

( * ) Notice: Subject to any disclaimer, the term of this patent is extended or adjusted under 35 U.S.C. 154(b) by 0 days.

(21) Appl. No.: 09/841,509

(22) Filed: Apr. 23, 2001

(51) Int. Cl.[7] .................................................. A61F 5/00
(52) U.S. Cl. ................... 602/4; 602/20; 602/5
(58) Field of Search .................... 602/4, 5–8, 19, 602/20; 128/96.1, 112.1, 115.1; 2/44, 45, 92

(56) References Cited

U.S. PATENT DOCUMENTS

| | | | |
|---|---|---|---|
| 2,415,288 A | 2/1947 | Jordan | |
| 3,307,538 A | 3/1967 | Groll | |
| 3,404,680 A | 10/1968 | Gutman et al. | |
| 3,548,818 A | 12/1970 | Kaplan | |
| 4,188,944 A | 2/1980 | Augustyniak | |
| 4,198,964 A | 4/1980 | Honneffer | |
| 4,232,664 A | 11/1980 | Blatt | |
| 4,327,909 A | 5/1982 | Neufeld | |
| 4,446,858 A | * 5/1984 | Verter | 602/4 |
| 4,622,961 A | 11/1986 | Christensen | |
| 4,878,490 A | 11/1989 | Scott | |
| 4,986,266 A | 1/1991 | Lindemann | |
| 5,018,513 A | * 5/1991 | Charles | 604/19 |
| 5,188,587 A | 2/1993 | McGuire et al. | |
| 5,334,132 A | * 8/1994 | Burkhead | 602/4 |
| 5,403,268 A | 4/1995 | Clement | |
| 5,628,725 A | 5/1997 | Ostergard | |
| 5,857,990 A | 1/1999 | Maas | |
| 6,110,133 A | * 8/2000 | Ritts | 602/4 |

\* cited by examiner

Primary Examiner—Michael A. Brown
Assistant Examiner—Laura M. Hamilton
(74) Attorney, Agent, or Firm—Carol D. Titus; James J. Leary (57) ABSTRACT

A sling having a generally rectangular shoulder pad with a cutout for the user's neck and four D-rings attached thereto is disclosed. A chest strap is attached to two of the D-rings, one on each end of the shoulder pad. An arm strap is attached to the two remaining D-rings. Both of the straps are formed of a resilient material to allow the user flexibility and mobility while wearing the sling. In order to create an easily adjusted attachment, each of the straps has a layer of resilient hook material on one side. At each end of each strap is a patch of hook material. The combination of hook and loop material is used to connect each end of the strap to the corresponding D-ring. An alternate embodiment uses two O-rings. Each O-ring attaches one end of both the arm strap and the chest strap to the shoulder pad. Also disclosed is a foam doughnut attachable to the underside of the shoulder pad to create a low pressure area within the opening in the doughnut to protecting a surgical site or other sensitive tissue.

23 Claims, 6 Drawing Sheets

DYNAMIC ARM SLING

FIELD OF INVENTION

The present invention relates generally to a sling for supporting the arm and shoulder of a patient. More particularly it relates to a sling that provides bracing and stabilization to the shoulder and arm of a patient. Although the sling may be used for other situations, the sling is particularly useful for acromio-clavicular separations.

BACKGROUND OF THE INVENTION

Slings of many different styles have been created to provide support while patients are recovering from broken bones, surgery and other injuries. However, these prior art devices have an assortment of disadvantages. For example, standard slings are made from inelastic materials. The user places their arm in the sling and the sling supports the weight of the arm. However, in this case, if the user moves the arm upward even a small amount, no support is provided. Therefore, most users are severely limited in the amount of motion they can achieve while they are incapacitated and using the sling.

Other styles of slings utilize complicated adjustment systems that are difficult to adjust to correctly fit the user and may be even more difficult for the user to don. These slings are also typically somewhat costly to manufacture due to the large number of parts and the assembly required.

Therefore, there is a clear need in the industry for an easily adjustable, resilient sling that provides elastic support for a user's arm throughout a wide range of motion, thereby enabling the user at least partial use of his or her arm.

SUMMARY OF THE INVENTION

The present invention takes the form of a sling to support and brace a user's arm after surgery or injury. The sling has a generally rectangular shoulder pad with a cutout for the user's neck and two to four attachment rings attached thereto. One embodiment uses four D-rings. A chest strap is attached to two of the D-rings, one on each end of the shoulder pad. An arm strap is attached to the two remaining D-rings. A second embodiment uses two O-rings in place of the four D-rings. Both the chest strap and the arm strap pass through each of the O-rings. Both of the straps are formed of a resilient or elastic material, such as neoprene to allow the user flexibility and mobility while wearing the sling. The resilient material allows the sling to provide more effective support for the user through a range of motions, thereby allowing increased activity while decreasing pain and the inconvenience associated with wearing a sling. In order to create an easily adjusted attachment, each of the straps has a layer of resilient hook material on one side. At each end of each strap is a patch of hook material. Optionally, the patch of hook material may extend beyond the end of the strap. The combination of hook and loop material is used to connect each end of the strap to the corresponding D-ring. Other attachment mechanisms, such as buckles, snaps, etc. may also be used.

If desired, a resilient pressure-relief member may be attached to the underside of the shoulder pad to create a low-pressure area within the opening in the doughnut. The doughnut would be useful in protecting surgical sites or other sensitive tissue from the pressure caused by the weight of the user's arm in the sling. The doughnut is preferably formed of a resilient material, such as foam, and has a layer of hook material on one side, which may be attached to the underside of the shoulder pad. If preferred, an alternate attachment could be used.

Other objects and advantages of the invention will no doubt occur to those skilled in the art upon reading and understanding the following detailed description along with the accompanying drawings.

DETAILED DESCRIPTION OF THE INVENTION

Figure 1:
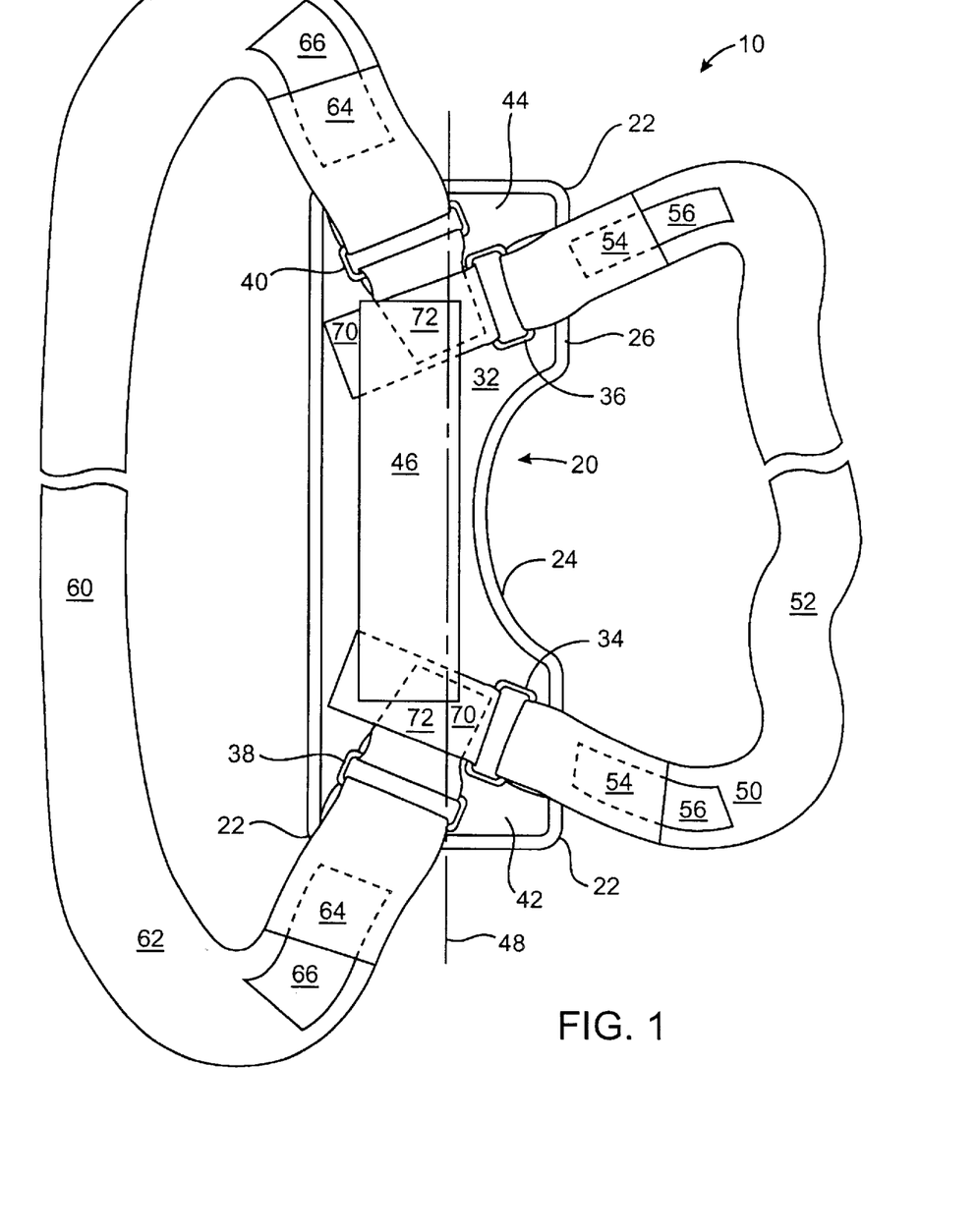
FIG. 1 is a top view of the sling.
Figure 2A:
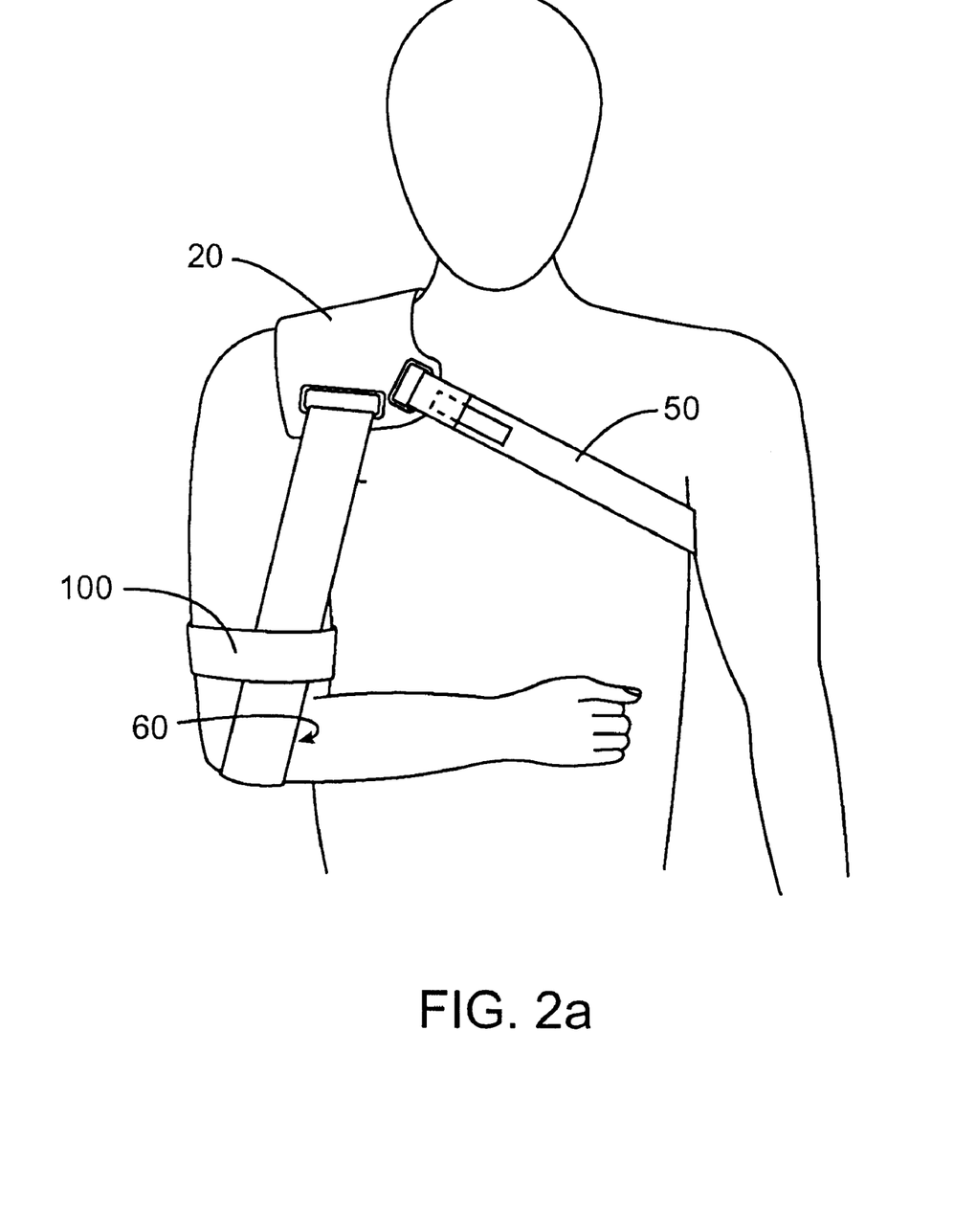
FIGS. 2a and 2b are front views of a user wearing the sling.
Figure 2B:
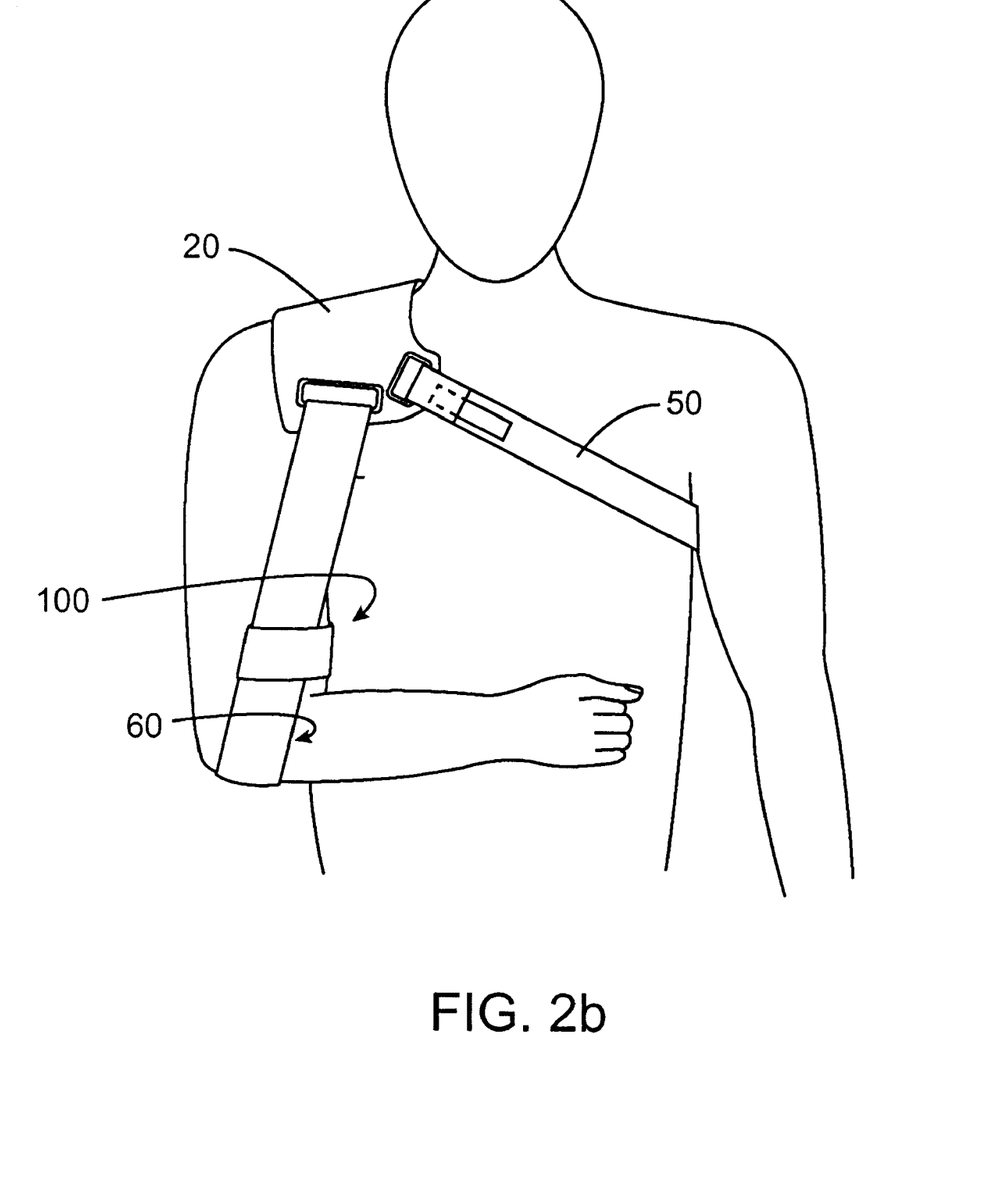

FIGS. 1, 2a and 2b show a top view of the sling 10 and a user wearing the sling, respectively. The sling 10 is formed of a shoulder pad 20 and two straps 50, 60. Although the shoulder pad 20 may be formed of different shapes such as rectangular or oval, the embodiment shown is rectangular with rounded corners 22 and an arcuate cutout 24 on one side. Preferably, the shoulder pad 20 is of sufficient length to extend down onto the user's chest and back. For most people a shoulder pad 20 with a length of 12 inches would be sufficient. However, larger and smaller version may be desirable for larger and smaller individuals including children. Therefore, versions of the shoulder pad 20 may be in the range of 24 inches to 6 inches, more preferably in the range of 8 to 18 inches, most preferably in the range of 10 to 15 inches in length. The cutout 24 is designed to rest against or near the user's neck. For the user's comfort, the edge of the shoulder pad 20 may optionally be trimmed with a smooth piping 26, as shown. The bottom surface 28 of the shoulder pad 20 may be formed of a loop material 30 so that it may mate with the hook material 84 on a pressure relief member 80, shown connected to the underside of the shoulder pad 20 in FIGS. 3 and 4. On the top surface 32 of the shoulder pad 20, four strap connection rings 34, 36, 38, 40 are attached. Optimally, the rings 34, 36, 38, 40 are attached at mirror image points on the two ends of the shoulder pad 20, thereby allowing the sling 10 to be used for either the right or the left shoulder. The embodiment shown uses plastic D-rings, however, other durable materials, such as metal, and ring styles may be used. The connection may also take other forms such as buckles, ties or other adjustable connections.

The shoulder pad 20 should be filled with a resilient material, such as foam, fiberfill, batting, etc., to promote the resilient support and to provide maximum comfort for the user. In order to hold the material in place within the shoulder pad 20, additional lines of stitching or tacking may be used during manufacturing or in the final product. Although other heights may be used, the thickness of the shoulder pad 20 is in the range of 0.1 to 2.0 inches, more preferably in the range of 0.25 to 1.5 inches, most preferably in the range of 0.5 to 1.25 inches. The current embodiment is approximately 1.0 inch thick.

Two straps are used in the present configuration: a chest strap 50 and an arm strap 60. Although the straps 50, 60 may be formed of other materials, they are optimally formed of a resilient or elastic material, such as neoprene. In order to facilitate easy attachment, one side of the strap 50, 60 may include a layer of resilient loop material 52, 62. The chest strap 50 is used to stabilize the shoulder pad 50 during use. The width of the chest strap 50 may be anywhere in the range of 0.5 to 5.0 inches, more preferably in the range of 1.0 to 3.0 inches, most preferably in the range of 1.0 to 2.0 inches. The embodiment show uses a chest strap 50 that is approximately 1.5 inches wide. The arm strap 60 is used to elastically support the user's arm. The width of the arm strap 60 is anywhere in the range of 1.0 to 6.0 inches, more preferably in the range of 1.5 to 4.0 inches, most preferably in the range of 1.5 to 3.0 inches. The embodiment shown uses an arm strap 60 that is approximately 2.0 inches wide. A patch of hook material 54, 64 is connected to each end of each strap 50, 60. If desired, the patch of hook material 54, 64 may extend beyond the end of the strap 50, 60 to create an extension 56, 66 that provides additional length and stability for the connection.

The two strap connection rings 34, 36 on the side of the shoulder pad 20 with the cutout 24 are for the chest strap 50. The chest strap 50 connection rings 34, 36 are preferably oriented such that the chest strap 50 extends from the longitudinal axis 48 of the shoulder pad 20 at an angle between 45 and 90 degrees, more preferably between 50 and 85, most preferably between 60 and 80. In the embodiment shown, the chest strap 50 extends at approximately a 70 degree angle from the longitudinal axis 48 of the shoulder pad 20. To connect an end of the chest strap 50 to a ring 34, 36, the user passes the end of the chest strap 50 through the ring 34, 36 from the under side of the ring 34, 36 and doubles it back. The patch of hook material 54 attached to the end of the chest strap 50 is connected with the mating loop material 52 that is attached to one side of the neoprene. The other end of the chest strap 50 is similarly attached to the other ring 34, 36. In alternate embodiments, one end of the chest strap 50 may be permanently attached to one of the rings 34, 36 or even directly to the shoulder pad 20.

The two strap connection rings 38, 40 located toward the straight edge of the shoulder pad 20 are for the arm strap 60. The arm strap 60 connection rings 38, 40 are preferably oriented such that the arm strap 60 extends from the longitudinal axis 48 of the shoulder pad 20 at an angle between 0 and 45 degrees, more preferably between 10 and 35 degrees, most preferably between 20 and 30 degrees. In the embodiment shown, the arm strap 60 extends at approximately a 25 degree angle from the longitudinal axis 48 of the shoulder pad 20. To connect an end of the arm strap 60 to a ring 38, 40, the user passes the end of the arm strap 60 through the ring 38, 40 from the under side of the ring 38, 40 and doubles it back. The patch of hook material 64 attached to the end of the arm strap 60 is connected with the mating loop material 62 that is attached to one side of the neoprene. The other end of the arm strap 60 is similarly attached to the other ring 38,40. In alternate embodiments, one end of the arm strap 60 may be permanently attached to one of the rings 38, 40 or even directly to the shoulder pad 20.

The strap connection rings 34, 36, 38, 40 may be attached to the shoulder pad 20 by any suitable means. In the embodiment shown, each ring 34,36, 38,40 has an attachment strip 70 of material passing therethrough. Both ends of each strip 70 are connected together and then stitched to the shoulder pad 20. To provide a secure connection, the attachment strips 70 for the arm strap connection rings 38, 40 and the chest strap attachment rings 34, 36 may create an overlap 72.

Additional reinforcing may also be used to secure the rings and provide structural support to hinder deformation of the shoulder pad 20. In FIG. 1, there is an additional reinforcing strap 46 stitched between the attachment strips 70 for the strap connection rings 34, 36, 38, 40 on the first end portion 42 and the second end portion 44 of the shoulder pad 20.

FIGS. 2a and 2b also show optional bicep straps 100. The strap attaches the arm strap 60 to the bicep of the user. If present, the bicep strap 100 may be permanently affixed to the arm strap or it may be releasably attached to the arm strap with hook fastener material or other convenient attachment means, such as buckles, snaps, ties, etc.

Figure 3:
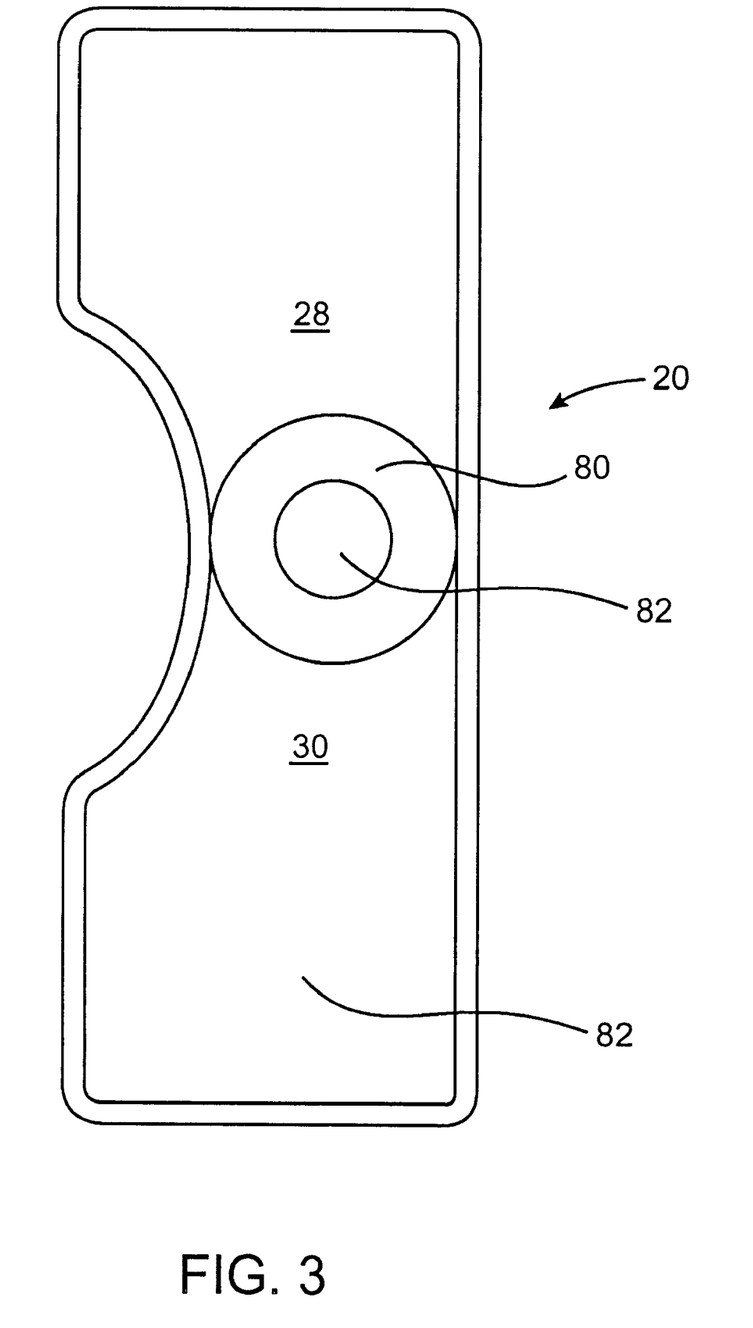
FIG. 3 shows the underside of the shoulder pad with the pressure relief doughnut.
Figure 4:
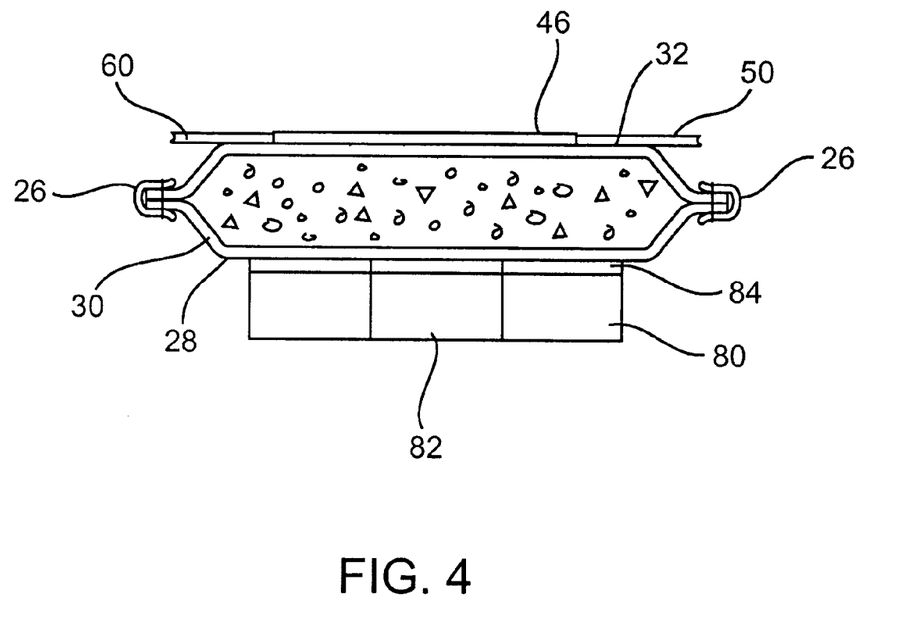
FIG. 4 is a cross-sectional view of the shoulder pad.
Figure 5:
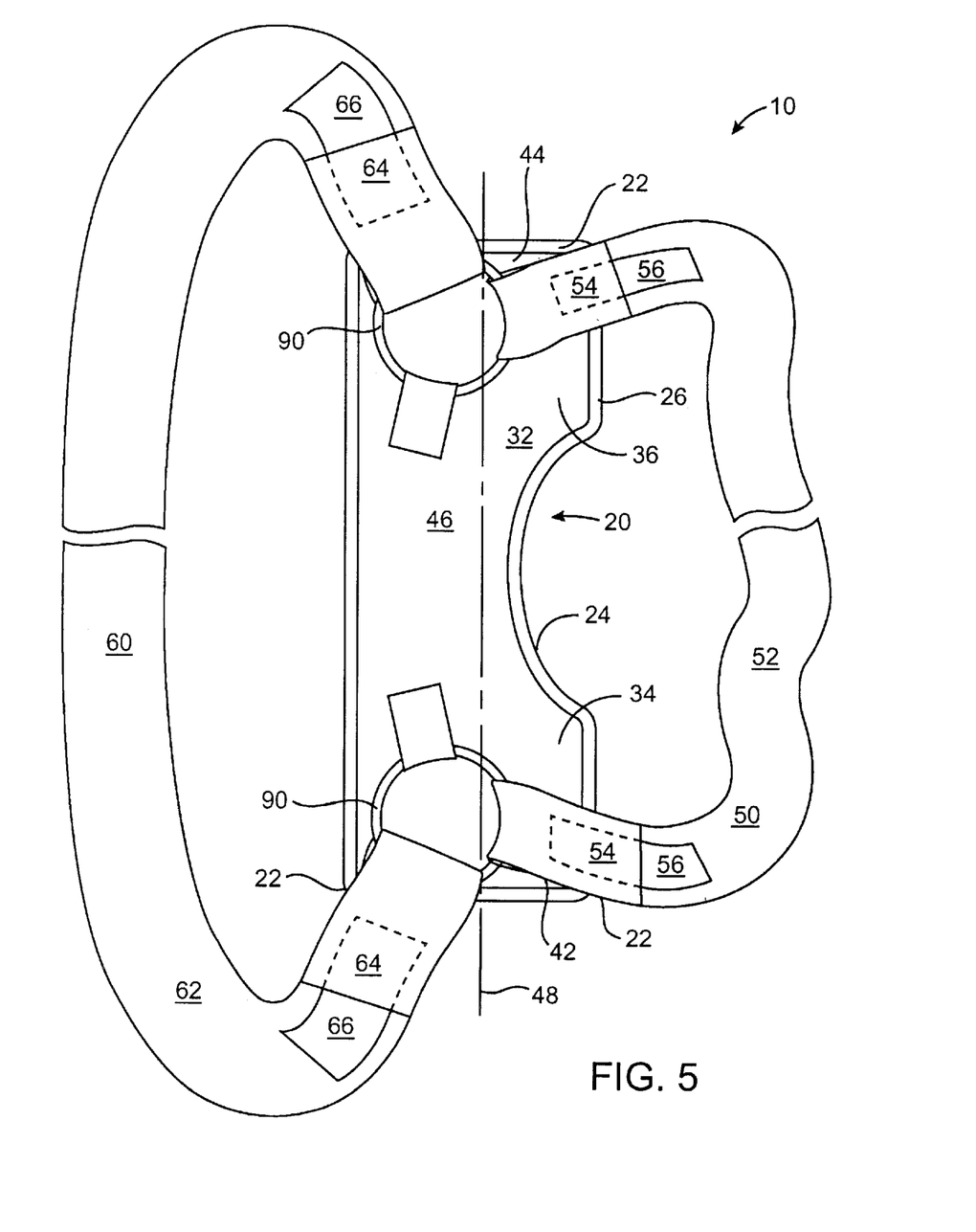
FIG. 5 is a top view of a second embodiment of the sling.

FIG. 3 shows the underside or bottom surface 28 of the shoulder pad 20 and FIG. 4 shows a cross-section thereof. The bottom surface 28 of the shoulder pad 20 is preferably formed of a loop material, thereby permitting attachment of a pressure relief member 80. The pressure relief member 80 shown is round and formed of a resilient foam with a layer of hook material 84 attached to one side. If preferred, the pressure relief member 80 may form different shapes such as oval, square, rectangular, etc. or some combination thereof. Also, alternate attachment mechanisms may be used. In alternate embodiments, the connection between the pressure relief member 80 and the shoulder pad 20 may be formed by other releasable attachments such as adhesive, snaps or other releasable attachment means. The pressure relief member 80 could ever. be held in place merely by the pressure of the sling 10.

The opening 82 in the center of the pressure relief member 80 provides an area where the pressure from the sling 10 is reduced or eliminated. Typically, the pressure relief member 80 is used in cases where the patient has a wound, abrasion or other sensitive site on which pressure is undesirable. In such a case, the physician or user can select the appropriate location for the pressure relief member 80 on the underside or bottom surface 28 of the shoulder pad 20 and attach the pressure relief member 80 with the mating parts of the hook and loop fastener, thereby temporarily affixing the pressure relief member 80 in the desired location. If, during use, the user finds that the pressure relief member 80 is improperly located due to the initial placement of the device 10 or due to other circumstances such as increased or decreased swelling, etc., the user may relocated the pressure relief member 80 in a more comfortable or more useful location.

In the embodiment shown, the sling 10 is symmetrical allowing the unit to function on either the left or the right side of the user without modification or adjustment of the sling 10. If preferred, left side and right side versions of the sling 10 may also be created. In this case, the end of one or both of the straps 50, 60 that are connected to the end of the shoulder pad 20 on the user's back could be permanently affixed to the shoulder pad 20. The adjustment for the strap 50, 60 lengths would be done exclusively by the opposite end of the straps 50, 60, which are attached to the front end of the shoulder pad 20 and would be within easy reach of the user.

The present invention is designed to provide almost infinite and constant adjustment by the user and/or doctor. A combination of the resiliency of the strap and the friction between the strap and the user's arm and/or sleeve securely supports the user's arm without slipping of the arm strap. The secure support allows the sling to provide constant, resilient support for the user when the arm and elbow are at their natural resting position angle of approximately 90 degrees and throughout a range of motion. Constant support allows a user to participate in more activities while providing the necessary support and protection and decreasing the pain and inconvenience.

As noted above, the particular configuration given is especially useful for treating patients with acromioclavicular separations. The pressure provided presses against the clavical, thereby moving it closer to its normal position proximate the acromium.

Many features have been listed with particular configurations, options and embodiments. Any one or more of the features described may be added to or combined with any of other embodiments or other standard devices to create alternate combinations and embodiments.

Although the examples given include many specificities, they are intended as illustrative of only a few possible embodiments of the invention. Other embodiments and modifications will, no doubt, occur to those skilled in the art. Thus, the examples given should only be interpreted as illustrations of a few preferred embodiments of the invention, and the full scope of the invention should be determined by the appended claims and their legal equivalents.

We claim:

1. A sling for supporting a user's arm, the sling comprising:
    a shoulder pad sized and configured to rest on the user's shoulder, said shoulder pad having a first end and a second end,
    a chest strap formed of a resilient material and having a first end and a second end,
    an arm strap formed of a resilient material and having a first end and a second end,
    a first attachment connecting said first end of said chest strap to said first end of said shoulder pad, said first attachment including:
        a first patch of hook material attached to said first end of said chest strap,
        and a first ring attached to said first end of said shoulder pad,
    a second attachment connecting said first end of said arm strap to said first end of said shoulder pad, said second attachment including:
        a second patch of hook material attached to said first end of said arm strap,
        and a second ring attached to said first end of said shoulder pad,
    a third attachment connecting said second end of said chest strap to said second end of said shoulder pad, said third attachment including:
        a third patch of hook material attached to said second end of said chest strap,
        and a third ring attached to said second end of said shoulder pad,
    and a fourth attachment connecting said second end of said arm strap to said second end of said shoulder pad, said fourth attachment including:
        a fourth patch of hook material attached to said second end of said arm strap,
        and a fourth ring attached to said second end of said shoulder pad,
wherein, when said sling is worn by the user, said first end of said chest strap passes through said first ring and said first patch of hook material is releasably attachable to a layer of loop material on said chest strap, and said first end of said arm strap passes through said second ring and said second patch of hook material is releasably attachable to a layer of loop material on said arm strap, and said second end of said chest strap passes through said third ring and said third patch of hook material is releasably attached to said layer of loop material on said chest strap, and said second end of said arm strap passes through said fourth ring and said fourth patch of hook material is releasably attached to said layer of loop material on said arm strap.

2. The sling of claim 1, wherein said first, second, third and fourth attachments are adjustable.

3. The sling of claim 1, wherein said rings are D-rings.

4. The sling of claim 1, wherein said rings are O-rings.

5. The sling of claim 1, wherein said straps are made of neoprene.

6. The sling of claim 1, further comprising a pressure relief member releasably attached to a bottom surface of said shoulder pad.

7. The sling of claim 6, wherein said pressure relief member is at least partially formed of foam.

8. The sling of claim 1, wherein said shoulder pad is generally rectangular with an arcuate cutout on one edge.

9. The sling of claim 1, wherein said arm strap extends downward from said shoulder pad.

10. The sling of claim 1, wherein said chest strap extends out from said shoulder pad at an angle to a longitudinal axis of said shoulder pad, said angle being in the range of 45 to 90 degrees.

11. The sling of claim 1, wherein said chest strap extends out from said shoulder pad at an angle to a longitudinal axis of said shoulder pad, said angle being in the range of 50 to 80 degrees.

12. The sling of claim 1, wherein said chest strap extends out from said shoulder pad at an angle to a longitudinal axis of said shoulder pad, said angle being in the range of 60 to 80 degrees.

13. The sling of claim 1, wherein said arm strap extends out from said shoulder pad at an angle to a longitudinal axis of said shoulder pad, said angle being in the range of 0 to 45 degrees.

14. The sling of claim 1, wherein said arm strap extends out from said shoulder pad at an angle to a longitudinal axis of said shoulder pad, said angle being in the range of 10 to 35 degrees.

15. The sling of claim 1, wherein said arm strap extends out from said shoulder pad at an angle to a longitudinal axis of said shoulder pad, said angle being in the range of 20 to 30 degrees.

16. The sling of claim 1, wherein said first attachment comprises:
    a first patch of hook material attached to said first end of said chest strap,
    and an O-ring attached to said first end of said shoulder pad,
    and said second attachment comprises:
        a second patch of hook material attached to said first end of said arm strap,
wherein, when said sling is worn by the user, said first end of said chest strap passes through said O-ring and said first patch of hook material is releasably attachable to a layer of loop material on said chest strap, and said first end of said arm strap passes through said O-ring and said second patch of hook material is releasably attachable to a layer of loop material on said arm strap.

17. The sling of claim 16, wherein said third attachment comprises:
    a third patch of hook material attached to said second end of said chest strap,
    and a second O-ring attached to said second end of said shoulder pad, and said fourth attachment comprises:
        a fourth patch of hook material attached to said second end of said arm strap, wherein, when said sling is worn by the user, said second end of said chest strap passes through said second O-ring and said third patch of hook material is releasably attached to said layer of loop material on said chest strap, and said second end of said arm strap passes through said second O-ring and said fourth patch of hook material is releasably attached to said layer of loop material on said arm strap.

18. A sling for supporting a user's arm, the sling comprising:
- a shoulder pad sized and configured to rest on the user's shoulder, said shoulder pad generally forming a rectangular shape and having a first end, a second end and an arcuate cutout in a long edge of the rectangle, said cutout sized and configured to accommodate at least a portion of the user's neck,
- a chest strap formed of a resilient material and having a first end and a second end,
- an arm strap formed of a resilient material and having a first end and a second end,
- a first attachment connecting said first end of said chest strap to said first end of said shoulder pad, said first attachment being adjustable and including:
  - a first patch of hook material attached to said first end of said chest strap,
  - and a first D-ring attached to said first end of said shoulder pad,
- a second attachment connecting said first end of said arm strap to said first end of said shoulder pad, said second attachment being adjustable and including:
  - a second patch of hook material attached to said first end of said arm strap,
  - and a second D-ring attached to said first end of said shoulder pad,
- a third attachment connecting said second end of said chest strap to said second end of said shoulder pad, said third attachment including:
  - a third patch of hook material attached to said second end of said chest strap,
  - and a third D-ring attached to said second end of said shoulder pad,
- and a fourth attachment connecting said second end of said arm strap to said second end of said shoulder pad, said fourth attachment including:
  - a fourth patch of hook material attached to said second end of said arm strap,
  - and a fourth D-ring attached to said second end of said shoulder pad, wherein, when said sling is worn by the user, said first end of said chest strap passes through said first D-ring and said first patch of hook material is releasably attached to a layer of loop material on said chest strap, and said first end of said arm strap passes through said second D-ring and said second patch of hook material is releasably attached to a layer of loop material on said arm strap, and said second end of said chest strap passes through said third D-ring and said third patch of hook material is releasably attached to said layer of loop material on said chest strap, and said second end of said arm strap passes through said fourth D-ring and said fourth patch of hook material is releasably attached to said layer of loop material on said arm strap.

19. The sling of claim 18, wherein said third and fourth attachments are adjustable.

20. The sling of claim 17, wherein said rings are O-rings.

21. The sling of claim 18, further comprising a pressure relief doughnut formed of a resilient material and releasably attached to a bottom surface of said shoulder pad.

22. The sling of claim 18, wherein said chest strap extends out from said shoulder pad at angle to the longitudinal axis of said shoulder pad, said angle being in the range of 50 to 85 degrees.

23. The sling of claim 18, wherein said arm strap extends out from said shoulder pad at angle to the longitudinal axis of said shoulder pad, said angle being in the range of 10 to 35 degrees.

* * * * *